US012686685B2

(12) United States Patent
Wang et al.

(10) Patent No.: US 12,686,685 B2
(45) Date of Patent: Jul. 21, 2026

(54) METHOD FOR LARGE-SCALE SYNTHESIS OF TETRODOTOXIN

(71) Applicants: Shanghai Shengping Medical Equipment Co., Ltd., Shanghai (CN); VastPro (Zhejiang) Technology Development Co., Ltd., Shanghai (CN); Zhejiang Boxiao Biopharmaceutical Co., Ltd., Hangzhou (CN)

(72) Inventors: Guangyin Wang, Shanghai (CN); Xiaoming Li, Shanghai (CN); Chengxi Wang, Shanghai (CN); Ping Huang, Shanghai (CN); Hua Bai, Shanghai (CN); Liang Lai, Shanghai (CN); Peng Guo, Shanghai (CN); Biao Jiang, Shanghai (CN); Wenfeng Zhu, Shanghai (CN)

(73) Assignees: Shanghai Shengping Medical Equipment Co., Ltd., Shanghai (CN); VastPro (Zhejiang) Pharmaceutical Co., Ltd., Shanghai (CN); Zhejiang Boxiao Biopharmaceutical Co., Ltd., Zhejiang (CN)

( * ) Notice: Subject to any disclaimer, the term of this patent is extended or adjusted under 35 U.S.C. 154(b) by 696 days.

(21) Appl. No.: 18/006,199

(22) PCT Filed: Jul. 19, 2021

(86) PCT No.: PCT/CN2021/107076

§ 371 (c)(1),
(2) Date: Jan. 20, 2023

(87) PCT Pub. No.: WO2022/017317

PCT Pub. Date: Jan. 27, 2022

(65) Prior Publication Data

US 2023/0312596 A1 Oct. 5, 2023

(30) Foreign Application Priority Data

Jul. 20, 2020 (CN) ........................ 202010699434.0

(51) Int. Cl.
*C07D 491/22* (2006.01)

(52) U.S. Cl.
CPC .................................. *C07D 491/22* (2013.01)

(58) Field of Classification Search
CPC .................................................. C07D 491/22
See application file for complete search history.

(56) References Cited

U.S. PATENT DOCUMENTS

2008/0145303 A1 6/2008 Hirota
2015/0190781 A1 7/2015 Hanamoto

FOREIGN PATENT DOCUMENTS

| | | | |
|---|---|---|---|
| CN | 101111454 | A | 1/2008 |
| CN | 107641128 | A | 1/2018 |
| WO | 2006080202 | A1 | 8/2006 |
| WO | 2013191269 | A1 | 5/2016 |

OTHER PUBLICATIONS

Kaestle, "Cleavage of Esters Using Carbonates and Bicarbonates of Alkali Metals: Synthesis of Thymopentin" Tetrahedron Letters, 1991, pp. 327-330.*
Katritzky, A. R.; Rogovoy, B.V. Arkivoc 2005, (iv) 49-87.*
Ohyabu Journal of the American Chemical Society, 2003, 125(29), 8798-8805.*
R. Sahai "Membrane Filtration" in Encyclopedia of Separation Science, 2000, p. 1717-1724.*
Brandt et al. "Practical Aspects of Preparative HPLC in Pharmaceutical and Development Production" LC•GC Europe Mar. 2-5, 2002.*
Maehara, Tomoaki; "Total Synthesis of (-)-Tetrodotoxin and 11-norTTX-6(R)-ol." Angewandte Chemie, International Edition, 56(6), 1549-1552 2017.*
Hawach Scientific, Shaanxi Province, P.R. China, Filter membrane page Online: "https://www.hawachmembrane.com/membranes-filters-mce-reg-cellulose-pes-and-ptfe/" accessed Feb. 26, 2026.*
International Search Report issued Oct. 20, 2021 in PCT/CN2021/107076.
Tomoaki Maehara, et al., "Total Synthesis of (-)-Tetrodotoxin and 11-norTTX-6(R)-ol," Angewandte Chemie, vol. 129, No. 6, pp. 24-29, Dec. 31, 2017.
Norio Ohyabu, et al., "First Asymmetric Total Synthesis of Tetrodotoxin," J.Am. Chem. Soc., vol. 29, No. 125, pp. 3798-8799, Jun. 28, 2003.
Wu, Wutong, "(non-official translation: Section 3, Microporous Membrane Filtration Technology)," (non-official translation: Biopharmaceutical Technology), pp. 324-326, Dec. 31, 2015.
Wang, Xiangyu, "(non-official translation: 5.4.1 Selection of Cellulose-Modified Iron Nanoparticles Removal Dye Types)," (non-official translation: Zero-Valent Molten Iron Nanoparticle Processing Technology in Environmental Engineering), p. 104, Dec. 31, 2016.
Written Opinion issued Oct. 20, 2021 in PCT/CN2021/107076.

(Continued)

*Primary Examiner* — David K O'Dell
(74) *Attorney, Agent, or Firm* — ICE MILLER LLP

(57) ABSTRACT

The present invention provides a method for biological and chemical synthesis of tetrodotoxin, specifically comprising the following steps: using cheap and easily available benzyl acetate as a raw material, and performing biological fermentation to obtain an optically pure intermediate ((5S, 6R)-5, 6-dihydroxycyclohexa-1, 3-dienyl) methyl acetate (formula I); and performing a series of chemical conversions on the intermediate to finally obtain tetrodotoxin at a purity of 95% or more without purifying the product. The present invention has the potential of large-scale production, and is an excellent alternative to the existing extraction method from a pufferfish.

11 Claims, No Drawings

(56) References Cited

OTHER PUBLICATIONS

Protective Groups in Organic Synthesis, 3rd Ed. pp 415-417 (1999).
Tomoaki Maehara, et al, "Total Synthesis of (-)- Tetrodotoxin and 11-norTTX-6(R)-ol," Agnew Chem, V. 129, pp. 1571-1574 (2017).

* cited by examiner

METHOD FOR LARGE-SCALE SYNTHESIS OF TETRODOTOXIN

CROSS-REFERENCE TO RELATED APPLICATION

This application is a Section 371 of International Application No. PCT/CN2021/107076 filed Jul. 19, 2021, which was published in the Chinese language Jan. 27, 2022, under International Publication No. WO 2022/017317 A1, which claims priority to Chinese Patent Application No. 202010699434.0 filed Jul. 20, 2020, the disclosures of which are incorporated herein by reference in their entireties.

TECHNICAL FIELD

The present disclosure belongs to the field of medicine and organic synthesis, and particularly related to a method of artificial synthesis for tetrodotoxin (TTX).

BACKGROUND

Tetrodotoxin (TTX) is an amino perhydroquinazoline type compound with a cage type orthoester inner salt structure, which is shown below:

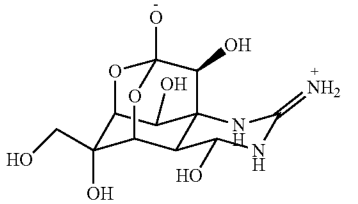

TTX

Tetrodotoxin is a white crystal, which is odorless and tasteless, and is slightly soluble in water, soluble in an acetic acid solution in water, but insoluble in an organic solvents: tertrodotoxin has a very special molecular structure, and it exists in a form of inner salt. Tetrodotoxin is a typical sodium ion channel blocker, which can selectively bind to the sodium channel receptors on the cell membrane surface of muscle and nerve cells. Tetrodotoxin has the effects of detoxification and analgesia without an addiction effect, and it as well exhibits the effects of hypotension, local anesthesia and tumor inhibition. In clinical application, the single dose of tetrodotoxin is extremely low, in a range of microgram. Therefore, the preparation for tetrodotoxin above gram level is of great significance for the development of its medicinal value.

The current source of tetrodotoxin is extraction from wild organisms. Tetrodotoxin's biological content is very small, and is generally in a magnitude order of 0.1-5 per million. Therefore, it is difficult to extract tetrodotoxin. For extraction, a large number of wild puffer fish are consumed, which is not beneficial to ecological environment protection, and the quality of extracted products is unstable. In addition, the extraction of tetrodotoxin from the corresponding artificial breeding organisms has not been successfully developed. At present, it is believed that by enriching natural toxins, wild animals can achieve 0.1-5 per million of tetrodotoxin in their bodies, which leads to the high price of tetrodotoxin, and limits its application in medicine and other fields.

The method of artificial total synthesis of tetrodotoxin started from the racemic compound reported by Kishi Research Group in 1972 (J. Am. Chem. Soc. 1972, 94, 9217-9219:9219-9221), and until 2018, when the present work began, there were more than ten research and development teams around the world studying the artificial synthesis of tetrodotoxin racemic compound, chiral pure compound and derivative products, and they had achieved a series of research progress and achievements. However, the steps of the synthesis method reported in the relevant work were lengthy (generally more than 30 steps), and the synthesis efficiency was very low, in which generally only 1-5 mg of samples can be obtained. In addition, considering the systematic error of the measurement method and the measurement equipment, there is no credibility on the yields reported in the associated works. Thus, the relevant work exhibits an academic exploration significance greater than its practical application value, and it does not have the value of large-scale tetrodotoxin synthesis and preparation as pharmaceutical raw materials. For example, the synthesis route reported by the Fukuyama research group (Angew: Chem. Int. Ed. 2017, 56, 1549-1552) is up to 31 steps, and specifically, many highly toxic chemicals and expensive chemical reagents are used in the last six steps. The purification process of related reactions is cumbersome, and tetrodotoxin cannot be prepared in a scale above gram level according to the c-GMP standard.

SUMMARY

In order to overcome the above mentioned technical problems, provided is a method for preparing tetrodotoxin represented by formula TTX in gram-grade, comprising: hydrogenating a compound of formula VI-a in a solvent to remove the protecting group Cbz, and then obtaining the tetrodotoxin after filtration and concentration,

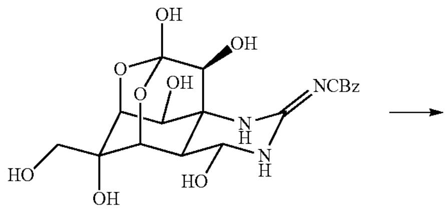

VI-a

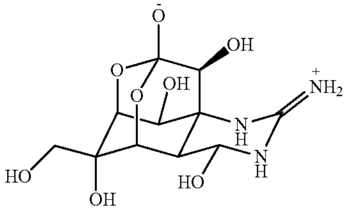

TTX wherein, Cbz represents benzyloxycarbonyl, and the solvent comprises but not limited to methanol, ethanol, ethyl acetate or isopropanol; an aqueous mixed fiber microporous membrane is used for the filtration.

In above mentioned method for preparing tetrodotoxin, the compound of formula VI-a can be obtained from a compound of formula V under a reaction with an acid:

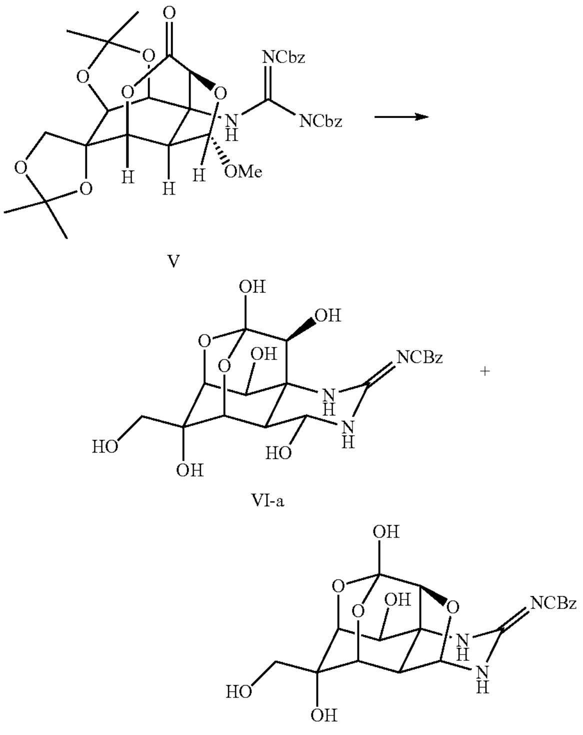

V

VI-a

VI-b wherein, the reaction affords the compound of formula VI-a and a compound of formula VI-b, and the compound of formula VI-a and the compound of formula VI-b are separated by a chiral preparative HPLC.

The compound of formula VI-b can be further converted into the compound of formula VI-a under a reaction with an acid:

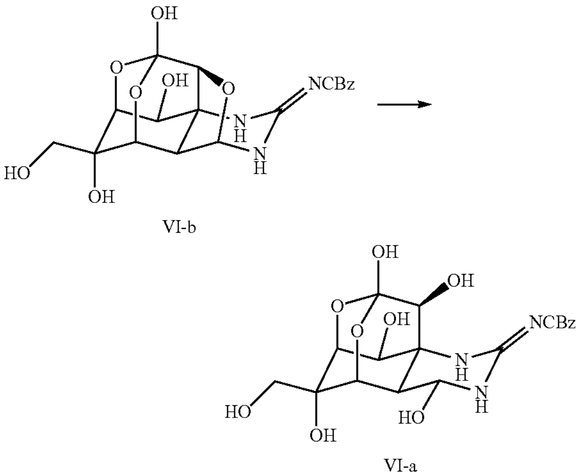

VI-b

VI-a wherein, the compounds of formula VI-a and formula VI-b are separated by a chiral preparative HPLC.

The compound of formula V can be obtained from a reaction between a compound of formula IV and Cbz-methylthiourea:

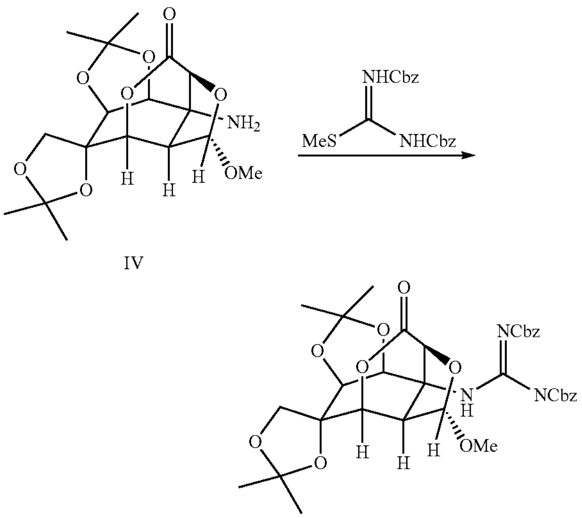

IV

V wherein, a metal Lewis acid, including lead chloride, lead acetate, silver nitrate, copper chloride and cuprous chloride, is used in the reaction.

The compound of formula IV can be obtained by removing Boc protecting group from a compound of formula III:

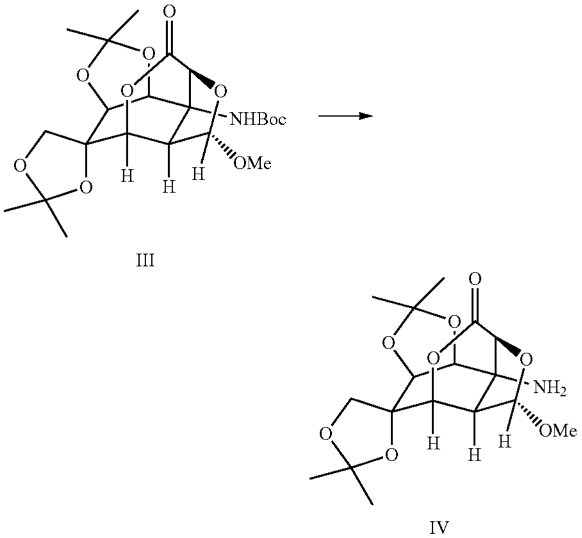

III

IV wherein, Boc represents tert butoxycarbonyl, acetonitrile is used as a solvent, trimethyliodosilane is used as a reagent, and the reaction temperature is from −10° C. to 50° C.

The compound of formula III can be obtained through intramolecular cyclization of a compound of formula II under a reaction with a base in a solvent:

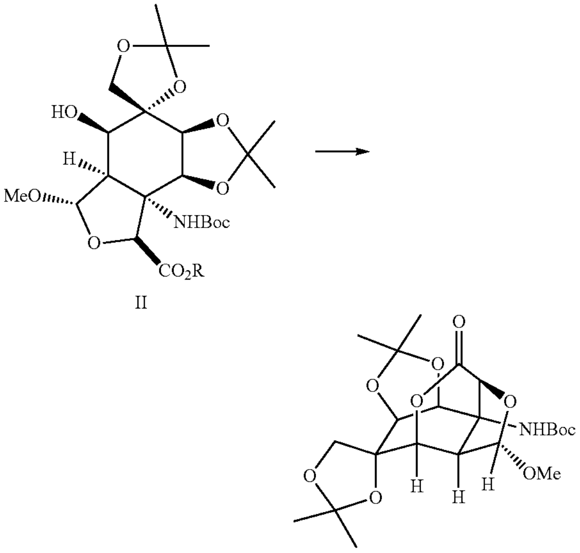

II

III wherein R is $C_{1-6}$ alkyl or substituted alkyl, and the base comprises potassium carbonate, sodium carbonate, potassium bicarbonate and sodium bicarbonate; the solvent comprises methanol, ethanol and toluene.

Further provided is a method for preparing tetrodotoxin (TTX) in grams, comprising steps (A)-(H):

(A) subjecting benzyl acetate to biotransformation to obtain an optically pure compound of formula I

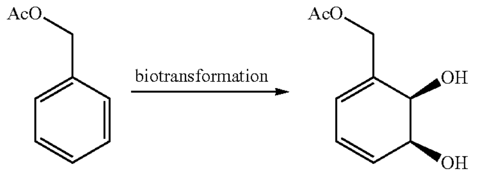

benzyl acetate I (B) subjecting the compound of formula I to a 19-step chemical conversion to obtain a compound of formula II

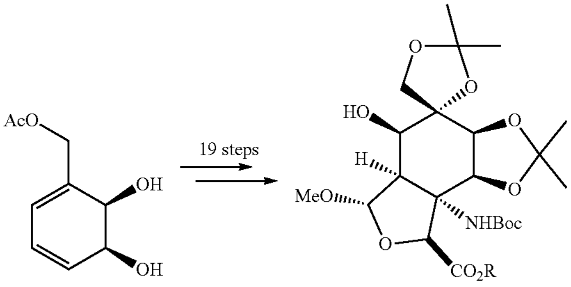

I II wherein R is $C_{1-6}$ alkyl or substituted alkyl.

(C) subjecting the compound of formula II to an intramolecular transesterification to obtain a compound of formula III

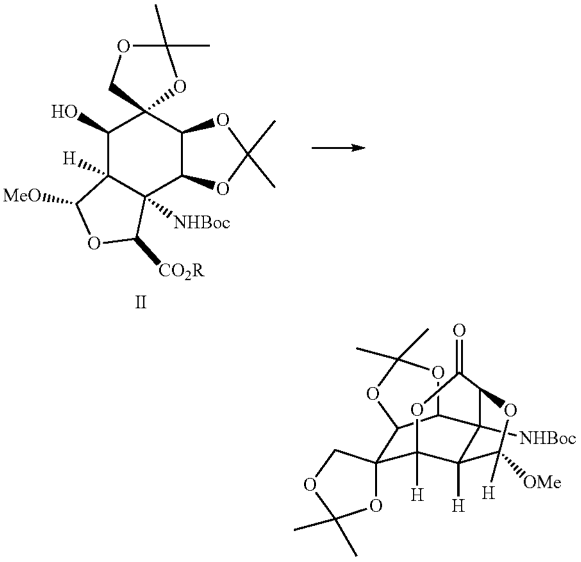

II

III (D) removing Boc protecting group from compound of formula III to obtain a compound of formula IV

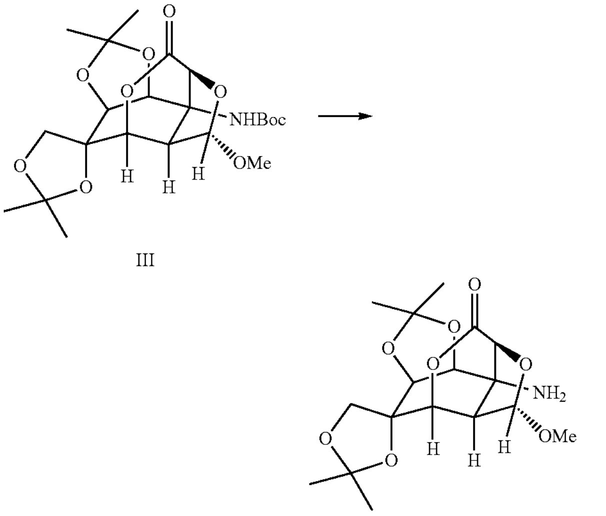

III

IV (E) reacting the compound of formula IV reacts with methylthiourea to obtain a compound of formula V

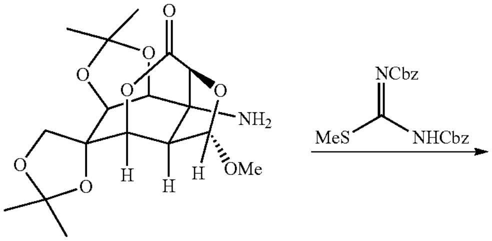

IV

-continued

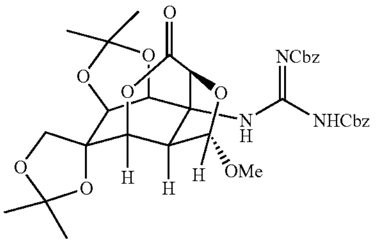

V (F) subjecting the compound of formula V to an intramolecular cyclization to obtain a compounds of formula VI-a and formula VI-b

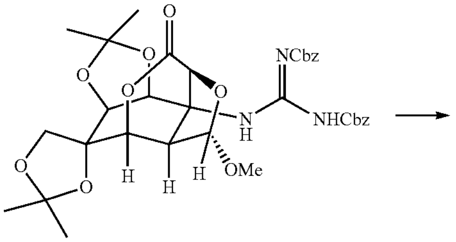

V

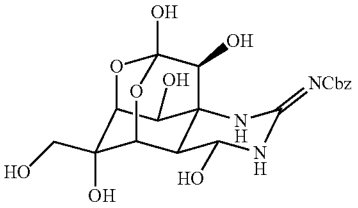

+

VI-a

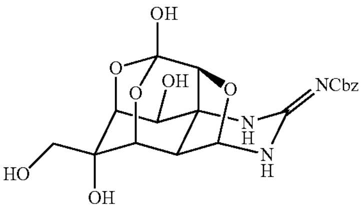

VI-b (G) hydrolyzing the compound of formula VI-b to obtain the compound of formula VI-a

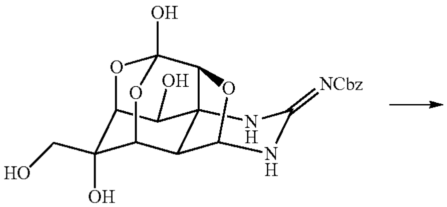

VI-b

-continued

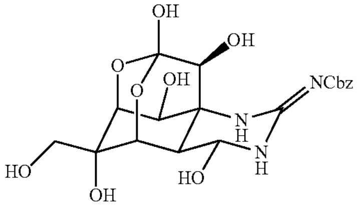

VI-a (H) subjecting the compound of formula VI-a to hydrogenation to remove Cbz protecting group to obtain a compound of formula TTX

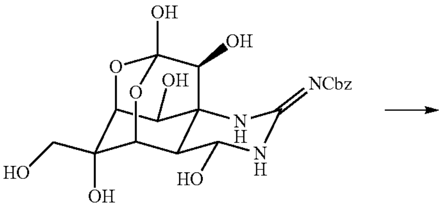

VI-a

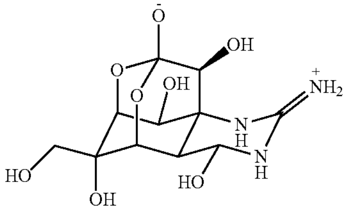

TTX

DETAILED DESCRIPTION

The technical content of the present disclosure are described through specific embodiments as follows. Those skilled in the art can easily understand other advantages and effects of the present disclosure according to the content disclosed in the specification. The present disclosure can also be implemented or applied by other different specific embodiments. Those skilled in the art can make various modifications and changes without departing from the spirit of the present disclosure.

General Terms and Definitions

Unless otherwise defined, all technical and scientific terms used herein have the same meaning as commonly understood by one of ordinary skill in the art to which this disclosure belongs. In case of any contradiction, the definition provided in this application shall prevail. When a trade name appears herein, it is intended to refer to its corresponding commercial product or its active ingredient. All patents, published patent applications, and publications cited herein are incorporated by reference.

When used in conjunction with a numerical variable, the terms "about" and "approximate" usually mean that the value of the variable and all values of the variable are within the experimental error (e.g. within the 95% confidence interval for the average) or within ±10% of the specified value, or within a wider range.

The terms "optional" or "optionally present" mean that the subsequently described event or circumstance may or may not occur, and that the description includes both the occurrence and the non-occurrence of said event or circumstance.

The expression "comprising" or the synonymous similar expressions "including", "containing" and "having" and the like are open-ended and do not exclude additional unrecited elements, steps or ingredients. The expression "consisting of" excludes any element, step or ingredient not specified. The expression "consisting essentially of" means that the scope is limited to the specified elements, steps or components, plus optional elements, steps or components that do not substantially affect the basic and novel characteristics of the claimed subject matter. It should be understood that the expression "comprising" encompasses the expressions "consisting essentially of" and "consisting of".

The term "one or more" or "at least one" may mean one, two, three, four, five, six, seven, eight, nine or more.

The ranges listed herein (such as numerical ranges) can cover each value in their ranges and each subranges formed by each value. For example, the expression "reaction temperature is from −20° C. to 25° C." covers every point value and subrange from −20° C. to 25° C., such as from −20° C. to 0° C., from 0° C. to 25° C., from −10° C. to 10° C., and -from 20° C., −10° C., 0° C., 5° C., 10° C., 15° C., 20° C., 25° C., etc. Other similar expressions, such as "at from-20° C. to 40° C." and "at from 0° C. to 100° C." and the like, should also be understood in a similar way. For example, the expression "molar equivalent is between 0.01-1.5" includes 0.01-0.1, 0.02-0.05, 0.03-0.05, 0.04-0.06, 0.1-0.5, 0.5-1.0, and 0.01, 0.03, 0.04, 0.05, 0.06, 0.07, 0.08, 0.09, 0.1, 0.2, 0.3, 0.4, 0.5, 1.0, etc.

Unless otherwise specified herein, singular references such as "a", "an", "the" include plural references. Unless otherwise stated, the concentration is calculated by weight, the proportion of liquid in mixed solution is calculated by volume, and the proportion (including percentage) of reaction reagent and compound is calculated by mole.

The protecting group derivative of the compound herein can be prepared by a method well known to those in the art. The protecting group in the protecting group derivative can be removed by a method well known to those in the art. The selection method of protecting groups and the detailed technical description of addition and removal of protecting groups can be seen in T.W. Greene, Protecting Groups in Organic Synthesis, 3rd edition, John Wiley & Sons, Inc. 1999.

The term "alkyl", as used herein alone or in combination with other groups, refers to a saturated straight chain, branched chain or cyclic hydrocarbon group. As used herein, the term "$C_{1-6}$ alkyl" refers to a saturated straight, branched chain or cyclic hydrocarbon group having 1-6 (e.g., 1, 2, 3, 4, 5 or 6) carbon atoms. For example, "$C_{1-6}$ alkyl" can be methyl, ethyl, n-propyl, isopropyl, n-butyl, isobutyl, sec-butyl, tert-butyl, n-pentyl, isopentyl, neopentyl, 3-methyl-pentan-3-yl, hexyl (e.g., n-hexyl, cyclohexyl, etc.). "$C_{1-6}$ alkyl" encompasses subranges therein, for example, "$C_{1-3}$ alkyl", "$C_{2-3}$ alkyl", "$C_{4-6}$ alkyl", etc.

Synthetic Routes and Intermediate Compounds

The disclosure relates to a method for preparing tetrodotoxin TTX in grams, which comprises the following steps (A)-(H):

Step (A): subjecting benzyl acetate to a biotransformation to obtain an optically pure compound of formula I

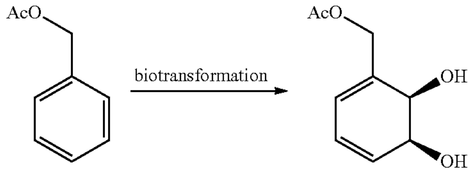

benzyl acetate I

This step of biotransformation mainly refers to the work of Hudlicky (Angew. Chem. Int. Ed. 2018, 57, 10994-10998), and the improvements from this work will be described in detail in another patent.

Step (B): subjecting the compound of formula I to a 19-step chemical conversion to obtain a compound of formula II

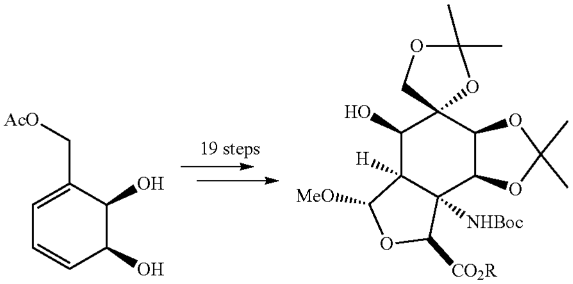

I II

This part mainly refers to the synthesis route of Hudlicky (Angew. Chem. Int. Ed. 2018, 57, 10994-10998) and Fukuyama (Angew. Chem. Int. Ed. 2017, 56, 1549-1552), wherein R is $C_{1-6}$ alkyl or substituted alkyl.

Step (C): subjecting the compound of formula II to an intramolecular transesterification to obtain a compound of formula III

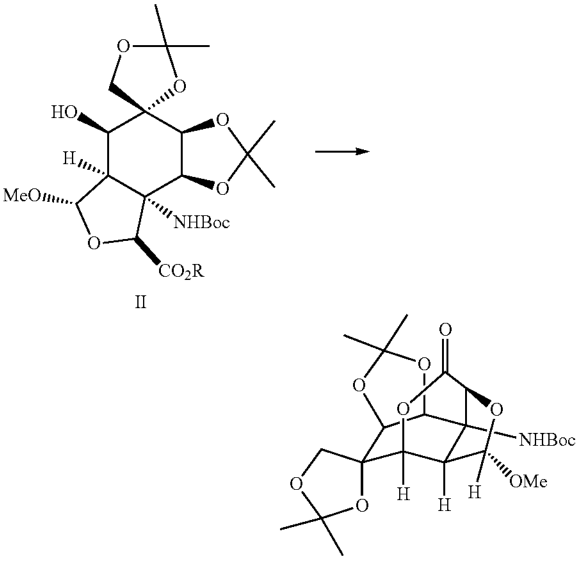

II

III

The compound of formula III is obtained by intramolecular cyclization of the compound of formula II under the action with a base. The base used in this reaction includes but not limited to potassium carbonate, sodium carbonate, potassium bicarbonate and sodium bicarbonate, wherein potassium carbonate is optimal; the solvent used in this reaction includes but not limited to methanol, ethanol and toluene, wherein methanol is optimal.

Step (D): removing Boc protecting group from the compound of formula III to obtain a compound of formula IV

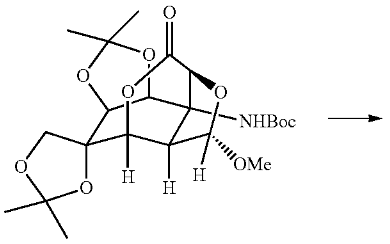

III

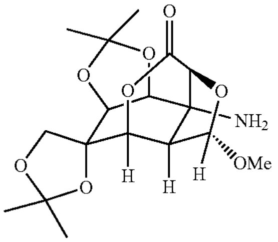

IV

The compound of formula IV is obtained by removing Boc protecting group from the compound of formula III. Acetonitrile is used as solvent, trimethyliodosilane is used as reagent, and the reaction temperature is from −10° C. to 50° C., wherein 0° C. is the optimal temperature.

Step (E): reacting the compound of formula IV with methylthiourea to obtain a compound of formula V

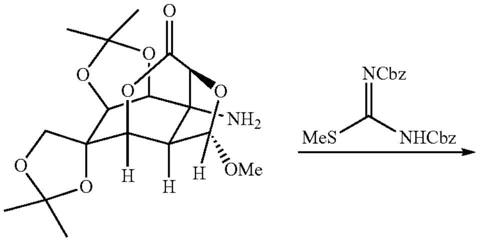

IV

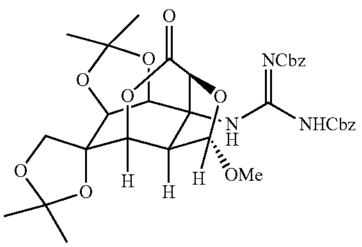

V

The compound of formula IV is reacted with Cbz methylthiourea to obtain a compound of formula V. A metal Lewis acid is used in the reaction, which includes but not limited to lead chloride, lead acetate, silver nitrate, copper chloride and cuprous chloride, avoiding the use of highly toxic mercury chloride, wherein copper chloride is optimal.

Step (F): subjecting the compound of formula V to an intramolecular cyclization to obtain a compound of formula VI-a and a compound of formula VI-b

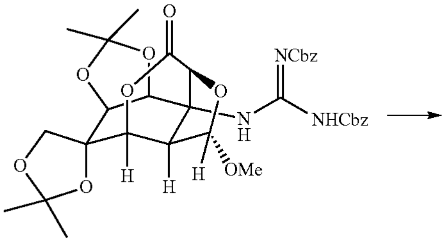

V

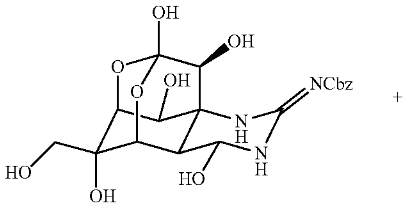

VI-a

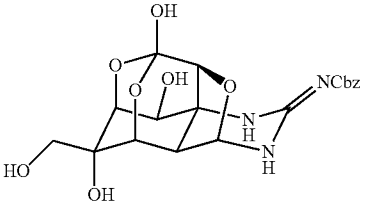

VI-b

Under the action with an acid, the compound of formula V is used to obtain a mixture of a compound of formula VI-a and a 4,9-dehydrated product of formula VI-b. Pure compounds of formula VI-a and formula VI-b are separated by a chiral preparative HPLC.

Step (G): hydrolyzing the compound of formula VI-b to obtain the compound of formula VI-a

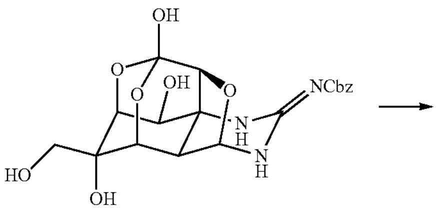

VI-b

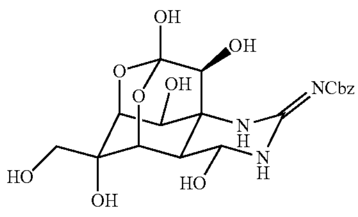

VI-a

The 4,9-dehydrated product of formula VI-b can be converted into the intermediate of formula VI-a in a certain proportion (1:8) under the action with an acid, and chiral preparation HPLC is used to obtain the partially pure formula VI-a. After 2 to 3 cycles, formula VI-b is converted to obtain formula VI-a in a yield of more than 80%.

Step (H): subjecting the compound of formula VI-a to hydrogenation to remove Cbz protecting group, to obtain the compound of formula TTX

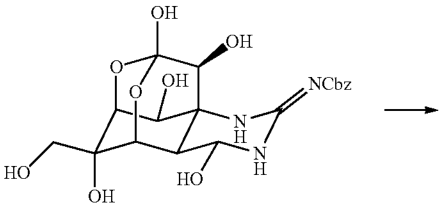

VI-a

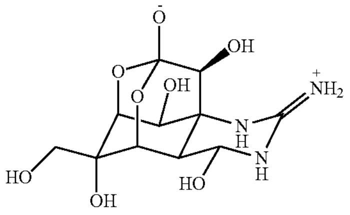

TTX

The protecting group Cbz can be removed by hydrogenation of formula VI-a, and the tetrodotoxin of formula TTX can be obtained with high purity through simple filtration and concentration. The solvent used in the reaction includes but not limited to methanol, ethanol, ethyl acetate or isopropanol, wherein methanol is optimal: aqueous mixed fiber microporous filter membrane is used for filtering, which can improve the filtering speed and effectively remove palladium-carbon.

Beneficial Effects

The technical problem to be solved by the present disclosure is to provide a method that does not depend on natural sources such as puffer fish, and can be used to synthesize tetrodotoxin on a large scale artificially, that is, a chemical method for gram scale synthesis of tetrodotoxin. Compared with the method reported in the prior art, the chemical synthesis method of present disclosure has an advantage that improvement of the synthesis method and purification method enables production of tetrodotoxin and its derivatives on a large scale according to the c-GMP standard gram level or above, which makes it possible to carry out clinical trials of tetrodotoxin as a candidate drug conforming to regulatory specifications. It has established a solid foundation for tetrodotoxin as an active pharmaceutical ingredients to become an important member in the field of human analgesic and detoxification drugs. Specifically, the advantages includes:

(1) Only one step of intramolecular transesterification is needed from II to III. Only one cheap and easily available base is used as a reagent. The reaction yield is equivalent to that of the original route. The two-step reaction in the original route and some expensive reagents have been replaced. The operability and large-scale repeatability of present reaction have been improved.

(2) From IV to V, non-toxic metal Lewis acid (such as $CuCl_2$) is used to replace the highly toxic $HgCl_2$ in the original route and the reaction is safer to operate and meets the API production requirements.

(3) Chiral preparative HPLC is used in the separation between VI-a and by-product VI-b, which exhibits good separation effect and can be used in preparation in large quantities, and it can replace the silica gel thin plate chromatography which is difficult to be used to scale up in the original route.

(4) By-product VI-b can be converted into VI-a under the action with a dilute acid. After one recycle, the total yield from V to VI-a is 68%, which is much higher than the yield of 41% of this step in the original route.

(5) An aqueous mixed fiber microporous membrane is used for filtering in the step from VI-a to TTX, which has a good effect of removing palladium-carbon. The filtrate can be evaporated to dryness without further purification to obtain TTX with a purity of 95% or more, avoiding the use of high pressure liquid chromatographic separation that is difficult to scale up in the original route.

(6) The present disclosure completes the synthesis of tetrodotoxin above gram level for the first time in the world, and the characterization data are complete and reliable, which can be used for large-scale preparation of tetrodotoxin material medicament (API) conforming to c-GMP standard, and this make it possible for tetrodotoxin as a candidate drug conforming to regulatory specifications to conduct clinical trials.

EXAMPLES

The following embodiments are only provided for illustrative purposes and should not be interpreted as limiting the present disclosure.

The NMR spectrum was recorded on the BRUKER AC 250 Fourier transform NMR spectrometer equipped with an Aspect 3000 computer and a 5 mm $^{1}H/^{13}C$ dual probe. The compounds were studied in a DMSO-$d^6$ (or $CDCl_3$) solution at a probe temperature of 313K. The instrument was locked on the deuterium signal of DMSO-$d^6$ (or $CDCl_3$). The chemical shift is expressed with distance in ppm from TMS in downfield which is an internal standard.

HPLC Conditions

The Agilent Technologies HPLC system equipped with Agilent Eclipse PLUS C18, 4.6*50 mm, 3.5 um column was used for analysis. In 3.5 minutes, a gradient elution from 95% 0.1% $H_3PO_4$ aqueous solution and 5% acetonitrile to 5% of 0.1% $H_3PO_4$ aqueous solution and 95% acetonitrile was performed, and continued elution of 5% of 0.1% $H_3PO_4$ aqueous solution and 95% acetonitrile for 1.5 minutes was performed. The flow rate was set as 2.0 mL/min. The column temperature was set at 35° C. The detection wavelength was 210 nm.

Chiral HPLC Conditions (Compounds VI-a and VI-b)

The Agilent Technologies HPLC system equipped with AD-H, 4.6*250 mm, 5 um column was used for analysis. In 25 minutes, 85% of 1% trifluoroacetic acid n-hexane solution and 15% of 1% trifluoroacetic acid ethanol solution was used for elution. The flow rate was set as 0.5 mL/min. The detection wavelength was 205 nm.

The raw materials, reagents and equipment used in the specific examples of the present disclosure are commercially available products. Reagents can be obtained from WuXi LabNetwork (Wuhan) Chemical Technology Co., Ltd., Shanghai Titan Scientific Co., Ltd., Sun Chemical Technology (Shanghai) Co., Ltd. and Shanghai Aladdin Biochemical Technology Co., Ltd.

Example 1: Preparation of Compound of Formula III

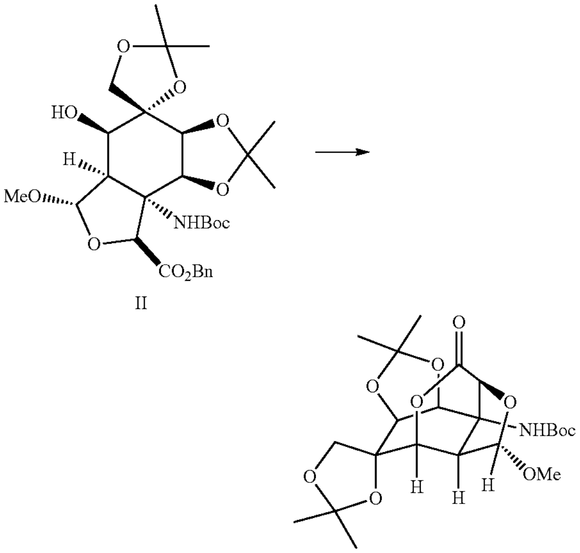

II

III 12 g of compound II and 6 g of potassium carbonate were dispersed in 300 ml of methanol at room temperature, stirred at room temperature for 18 hours, the raw materials disappeared which was detected by HPLC, and then filtered to remove the precipitate and the filtrate was submitted to rotatory for evaporation at room temperature to remove most of the methanol. Then 300 ml of water was added, and the solution was extracted for three times with 300 ml of ethyl acetate. The organic phase was combined, and dried over with anhydrous sodium sulfate, and then filtered, spun to dry, and then purified by ethyl acetate petroleum ether (1:3) silica gel column chromatography to obtain a white foam solid compound III (7.3 g, yield 75%). 1H NMR ($CDCl_3$, 400 MHz): δ 5.16 (s, 1H), 5.02 (d, J=6.9 Hz, 1H), 5.01 (s, 1H), 4.42 (s, 1H), 4.41 (d, J=6.9 Hz, 1H), 4.37 (d, J=10.1 Hz, 1H), 4.32 (s, 1H), 4.25 (d, J=10.1 Hz, 1H), 3.48 (br s, 1H), 3.44 (s, 3H), 1.46 (s, 9H), 1.43 (s, 3H), 1.38 (s, 3H), 1.29 (s, 3H).

Example 2: Preparation of Compound of Formula IV

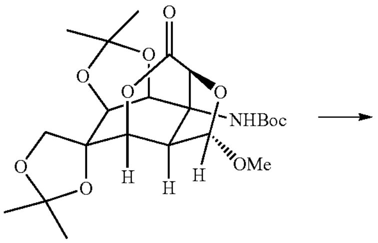

III

-continued

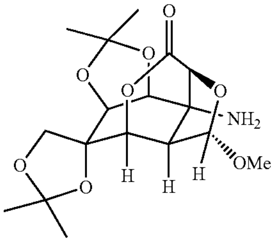

IV 180 ml of the freshly prepared TMSI solution (0.32 M) was added to 240 ml of anhydrous acetonitrile solution of 6.9 g of compound III under the ice bath. The mixture was reacted at room temperature for 15 minutes, and 450 ml of sodium thiosulfate solution was added to quench the reaction. The mixture was respectively extracted for three times with 450 ml of chloroform methanol (9:1) mixed solvent, and then the organic phase was combined and dried over with anhydrous sodium sulfate, and then filtered and concentrated to obtain crude compound IV (5.4 g), which was directly put into the next step of reaction without further purification. 1H NMR ($CDCl_3$, 400 MHz): δ 6.34 (br, 2H), 5.32 (d, J=7.2 Hz, 1H), 5.30 (s, 1H), 4.79 (d, J=1.2 Hz, 1H), 4.42 (d, J=7.6 Hz, 1H), 4.39 (s, 1H), 4.38 (d, J=10.0 Hz, 1H), 4.28 (d, J=10.4 Hz, 1H), 3.57 (s, 3H), 3.36 (t, J=2.0 Hz, 1H), 2.03 (d, J=8.0 Hz, 1H), 1.46 (s, 3H), 1.44 (s, 6H), 1.38 (s, 3H), 1.36 (s, 3H).

Example 3: Preparation of Compound of Formula V

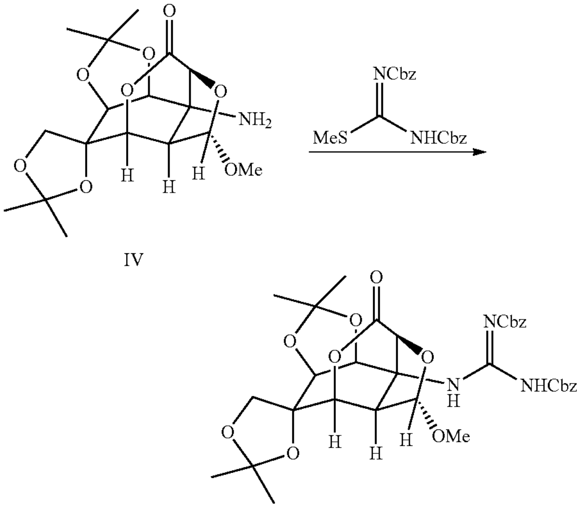

IV

V 15 g of copper chloride was added to 240 ml of dichloromethane solution with 5.4 g of crude compound IV, 15 ml of triethylamine and 10 g of Cbz methylthiourea at room temperature, and then the mixture was reacted at room temperature for 5 hours. 450 ml of water was added to quench the reaction, and then extracted for three times with 200 ml of dichloromethane, and then dried over with anhydrous sodium sulfate, and then filtered and concentrated. White foam solid compound V (8.58 g, two-step yield of 86%) was obtained through petroleum-ether ethyl acetate silica gel column chromatography (3:1). 1H NMR ($CDCl_3$, 400 MHz): δ 11.7 (s, 1H), 8.8 (s, 1H), 7.38-7.30 (m, 10H), 5.24 (d, J=7.8 Hz, 1H), 5.21 (s, 1H), 5.18 (d, J=13.0 Hz, 1H), 5.13 (s, 1H), 5.04 (d, J=13.0 Hz, 1H), 4.58 (s, 1H), 4.47 (d, J=7.8 Hz, 1H), 4.31 (s, 1H), 4.28 (s, 2H), 3.91 (s, 1H), 3.25 (s, 3H), 1.36 (s, 3H), 1.31 (s, 3H), 1.24 (s, 3H), 1.21 (s, 3H)

Example 4: Preparation of Compounds of Formula VI-a and Formula VI-b

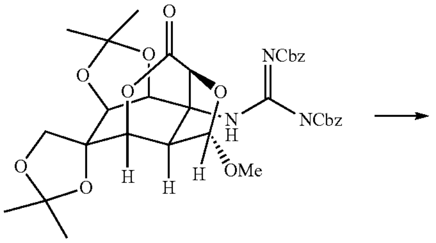

V

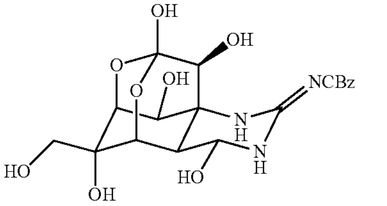

+

VI-a

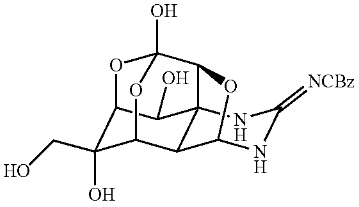

VI-b 7.48 g of compound V was dissolved in a mixed solvent containing 70 ml of trifluoroacetic acid and 70 ml of water at room temperature, and then the solution was heated at 60° C. to react for 18 hours. HPLC detected that the raw material reacted completely. Then then reaction solution was concentrated at 50° C. and dried, and then chiral preparative HPLC (Chiralpak AD-H, n-Hexane:ETOH=75:25) was used to obtain white solid compound VI-a (2.28 g, yield: 46%) and compound VI-b (1.28 g, yield: 27%). Compound VI-a: 1H NMR ($CD_3OD$, 400 MHz): δ 7.39-7.29 (m, 5H), 5.56 (s, 1H), 5.09 (m, 2H), 4.48 (d, J=1.8 Hz, 1H), 4.17 (m, 2H), 4.02 (m, 2H), 3.93 (m, 2H), 2.26 (d, J=9.2 Hz, 1H): Compound VI-b: 1H NMR ($CD_3OD$, 400 MHz): δ 7.38-7.26 (m, 5H), 5.28 (s, 1H), 5.07 (s, 2H), 4.48 (d, J=1.8 Hz, 1H), 4.42 (s, 1H), 4.16 (br s, 1H), 4.02 (d, J=1.8 Hz, 1H), 3.97 (d, J=11.9 Hz, 1H), 3.90 (d, J=11.9 Hz, 1H), 2.70 (d, J=2.8 Hz, 1H).

Example 5: Recycling of Compound of Formula VI-b

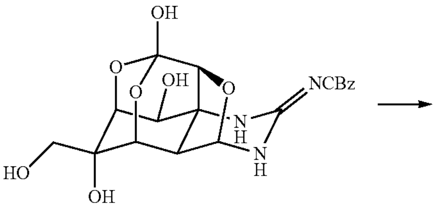

VI-b

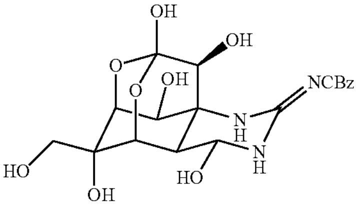

VI-a 1.28 g of compound V was dissolved in a mixture of 7 ml of trifluoroacetic acid and 70 ml of water at room temperature, and then the solution was heated at 60° C. to react for 24 hours. HPLC detected that the proportion of compound VI-a and compound VI-b was constant. The reaction solution was concentrated at 50° C. and dried, and then chiral preparative HPLC (Chiralpak AD-H, n-Hexane:ETOH=75:25) was used to obtain white solid compound VI-a (1.13 g, yield: 88%) and compound VI-b (0.14 g, yield: 12%).

Example 6: Preparation of Compound of Formula TTX

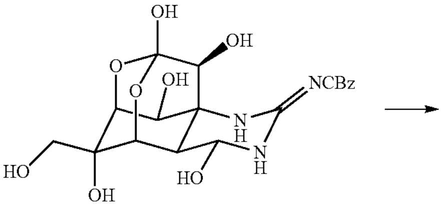

VI-a

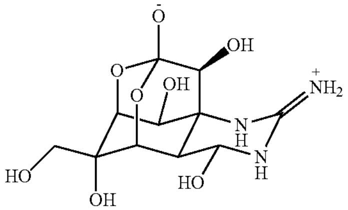

TTX 500 mg of 10% wet palladium-carbon was added to 150 ml methanol solution of 2.39 g compound VI-a at room temperature, the mixture was hydrogenated for 3 hours. HPLC detected that the raw material reaction was complete. The catalyst was removed through microporous membrane filtration, and the filter cake was washed with 500 ml of 0.05 M acetic acid aqueous solution, and the compound TTX (1.65 g, 98%) was obtained after the filtrate was concentrated at 45° C. under reduced pressure. $[\alpha]_D^{23}$ −10.4° (c 0.25, 0.05 M AcOH); IR (neat, cm-1): 3211, 1658, 1608, 1186, 1126, 1076, 979; $^1$HNMR (1% $CF_3COOD$/4% $CD_3COOD$/95% $D_2O$, 400 MHz): δ 5.49 (d, J=9.6 Hz, 1H), 4.27 (br s, 1H), 4.23 (br s, 1H), 4.06 (s, 1H), 4.02 (d, J=7.0 Hz, 1H), 4.00 (d, J=7.0 Hz, 1H), 3.94 (s, 1H), 2.33 (d, J=9.6 Hz, 1H); $^{13}$CNMR (1% $CF_3COOD$/4% $CD_3COOD$/95% $D_2O$, 100 MHz): δ 156.7 (C), 110.9 (C), 79.8 (CH), 75.2 (CH), 74.0 (CH), 72.9 (CH), 71.6 (C), 71.0 (CH), 65.6 (CH), 59.8 (C), 40.8 (CH); HRMS (ESI$^+$): Calcd for $C_1H_{18}N_3O_8$ ($[M+H]^+$): 320.1094, Found: 320.1094. All the analysis data were consistent with the literature reports.

Although the disclosure has elaborated and described typical embodiments, the disclosure is not limited to the details. Since various possible modifications and substitutions do not deviate from the spirit of the disclosure, those skilled in the art can use the variants and equivalents of the disclosure that can be thought of by conventional experiments, so all these variants and equivalents fall within the spirit and scope of the present disclosure as defined by the following claims.

The invention claimed is:

1. A method for preparing tetrodotoxin represented by formula TTX, comprising:

(1) subjecting a compound of formula II to an intramolecular cyclization with a base in a solvent to obtain a compound of formula III:

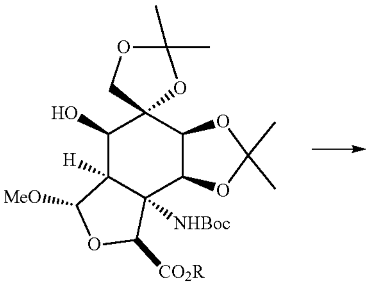

II

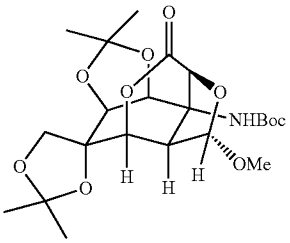

III wherein R is $C_{1-6}$ alkyl or substituted alkyl, and the base is selected from the group consisting of potassium carbonate, sodium carbonate, potassium bicarbonate and sodium bicarbonate; and the solvent is selected from the group consisting of methanol, ethanol and toluene;

(2) removing Boc protecting group from the compound of formula III to obtain a compound of formula IV:

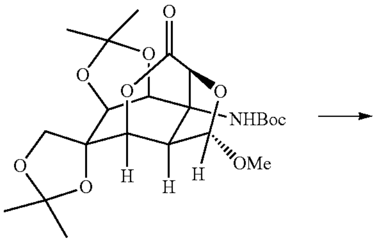

III

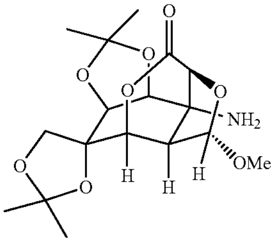

IV (3) reacting the compound of formula IV with Cbz methylthiourea to obtain a compound of formula V:

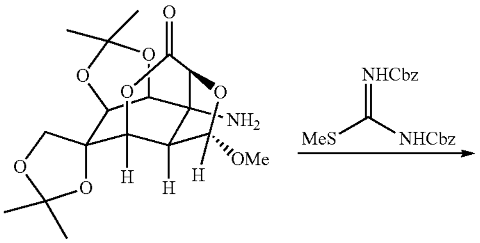

IV

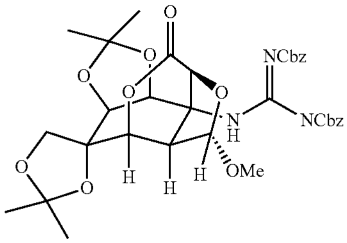

V wherein, a metal Lewis acid is used in the reaction;

(4) subjecting the compound of formula V to a molecular cyclization to obtain a compound of formula VI-a and a compound of formula VI-b:

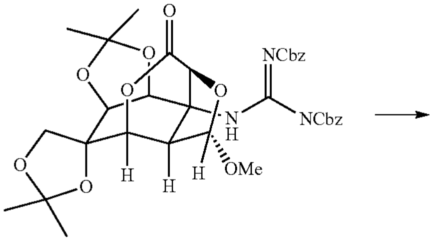

V

-continued

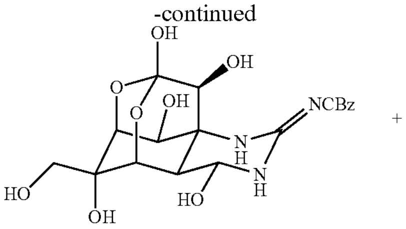

VI-a

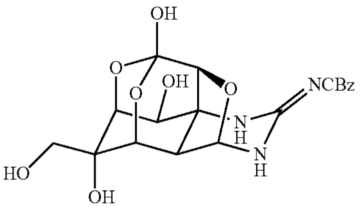

VI-b wherein, the compound of formula VI-a and the compound of formula VI-b are separated by a chiral preparative HPLC;

(5) hydrolyzing the compound of formula VI-b to obtain the compound of formula VI-a:

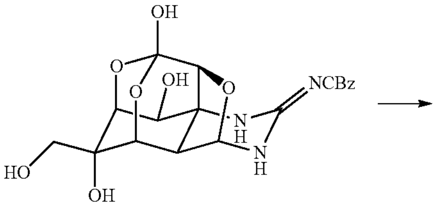

VI-b

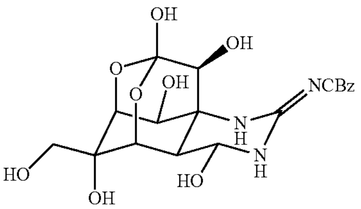

VI-a wherein, the compound of formula VI-a and the compound of formula VI-b are separated by a chiral preparative HPLC; and (6) hydrogenating the compound of formula VI-a in a solvent to remove the protecting group Cbz, and then obtaining the tetrodotoxin after filtration and concentration,

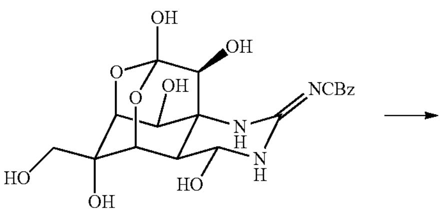

VI-a

-continued

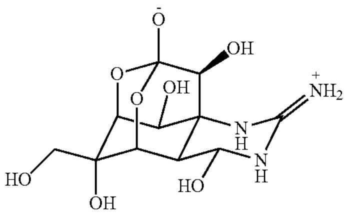

TTX wherein, Cbz represents benzyloxycarbonyl, and the solvent is selected from the group consisting of methanol, ethanol, ethyl acetate and isopropanol.

2. The method for preparing tetrodotoxin according to claim 1, further comprising using an aqueous mixed fiber microporous filter membrane for the filtration.

3. The method for preparing tetrodotoxin according to claim 1, wherein, the molecular cyclization in step (4) is carried out with an acid.

4. The method for preparing tetrodotoxin according to claim 3, wherein, the reaction in step (5) is carried out with an acid.

5. The method for preparing tetrodotoxin according to claim 1, wherein, the metal Lewis acid in step (3) is copper chloride.

6. The method for preparing tetrodotoxin according to claim 5, wherein, in the step (2) reaction, acetonitrile is used as a solvent, trimethyliodosilane is used as a reagent, and the reaction temperature is from −10° C. to 50° C.

7. The method for preparing tetrodotoxin according to claim 6, wherein, the reaction temperature is 0° C.

8. The method for preparing tetrodotoxin according to claim 1, wherein, in step (1), the base is potassium carbonate and the solvent is methanol.

9. A method for preparing tetrodotoxin, comprising the following steps:

(1) subjecting a compound of formula II to an intramolecular cyclization with a base in a solvent to obtain a compound of formula III;

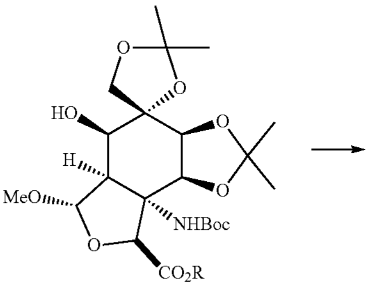

II

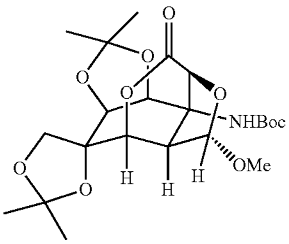

III wherein R is $C_{1-6}$ alkyl or substituted alkyl, and the base is selected from the group consisting of potassium carbonate, sodium carbonate, potassium bicarbonate and sodium bicarbonate; and the solvent is selected from the group consisting of methanol, ethanol and toluene;

(2) removing Boc protecting group from the compound of formula III to obtain a compound of formula IV:

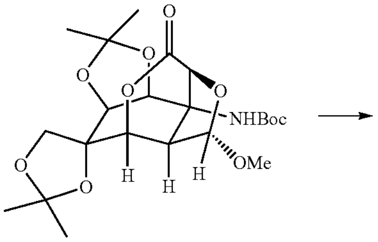

III

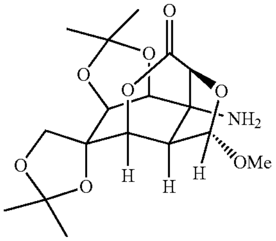

IV wherein, acetonitrile is used as a solvent, trimethyliodosilane is used as a reagent, and the reaction temperature is from −10° C. to 50° C.;

(3) reacting the compound of formula IV with Cbz methylthiourea to obtain a compound of formula V

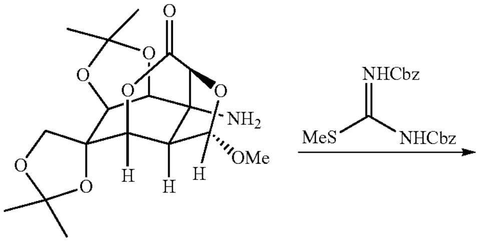

IV

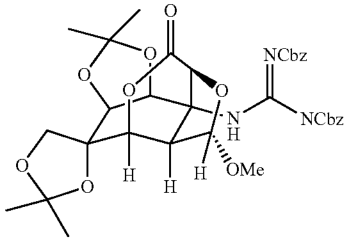

V wherein, a metal Lewis acid is used in the reaction;

(4) subjecting the compound of formula V to a molecular cyclization to obtain a compound of formula VI-a and a compound of formula VI-b

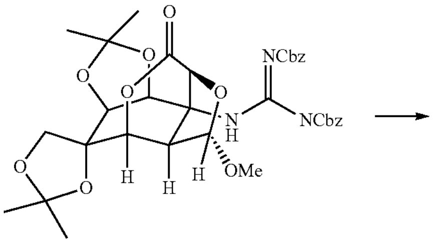

V

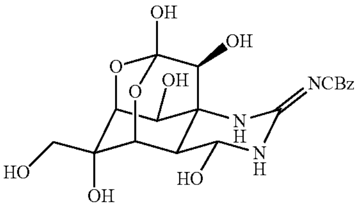

VI-a

+

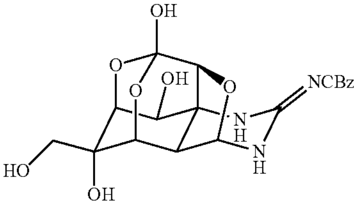

VI-b wherein, the compound of formula VI-a and the compound of formula VI-b are separated by a chiral preparative HPLC;

(5) hydrolyzing the compound of formula VI-b to obtain the compound of formula VI-a

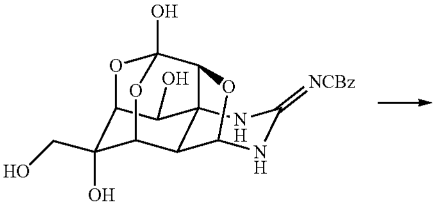

VI-b

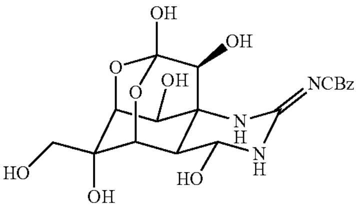

VI-a wherein, the compound of formula VI-a and the compound of formula VI-b are separated by a chiral preparative HPLC; and (6) subjecting the compound of formula VI-a to hydrogenation in a solvent to remove Cbz protecting group to obtain a compound of formula TTX after filtration

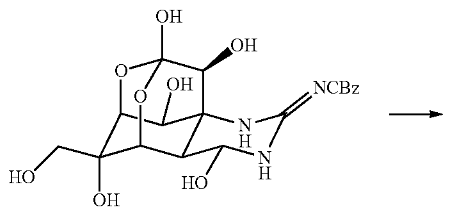

VI-a

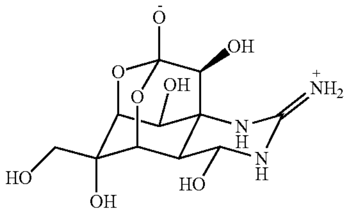

TTX wherein, Cbz represents benzyloxycarbonyl, and the solvent is selected from the group consisting of methanol, ethanol, ethyl acetate and isopropanol; and an aqueous mixed fiber microporous filter membrane is used for the filtration.

10. The method for preparing tetrodotoxin according to claim 1, wherein, the metal Lewis acid is selected from the group consisting of lead chloride, lead acetate, silver nitrate, copper chloride and cuprous chloride.

11. The method for preparing tetrodotoxin according to claim 9, wherein, the metal Lewis acid is selected from the group consisting of lead chloride, lead acetate, silver nitrate, copper chloride and cuprous chloride.

* * * * *